US008961383B2

(12) United States Patent
Parsai et al.

(10) Patent No.: US 8,961,383 B2
(45) Date of Patent: Feb. 24, 2015

(54) INTRACAVITARY RADIATION SYSTEM

(75) Inventors: E. Ishmael Parsai, Sylvania, OH (US); John J. Feldmeier, Monroe, MI (US)

(73) Assignee: The University of Toledo, Toledo, OH (US)

( * ) Notice: Subject to any disclaimer, the term of this patent is extended or adjusted under 35 U.S.C. 154(b) by 584 days.

(21) Appl. No.: 12/595,329

(22) PCT Filed: Apr. 9, 2008

(86) PCT No.: PCT/US2008/004550
§ 371 (c)(1),
(2), (4) Date: Nov. 4, 2009

(87) PCT Pub. No.: WO2008/124149
PCT Pub. Date: Oct. 16, 2008

(65) Prior Publication Data
US 2010/0069878 A1 Mar. 18, 2010

Related U.S. Application Data

(60) Provisional application No. 60/922,726, filed on Apr. 10, 2007.

(51) Int. Cl.
A61M 31/00 (2006.01)
A61M 25/10 (2013.01)
A61N 5/10 (2006.01)
A61M 25/00 (2006.01)

(52) U.S. Cl.
CPC ....... *A61M 25/1002* (2013.01); *A61M 25/1011* (2013.01); *A61M 2025/0034* (2013.01); *A61M 2025/0036* (2013.01); *A61M 2025/004* (2013.01); *A61M 2025/1013* (2013.01); *A61M 2025/1015* (2013.01); *A61N 5/1016* (2013.01); *A61N 2005/1018* (2013.01)
USPC ............................................ 600/3

(58) Field of Classification Search
CPC .................... A61N 5/1015; A61N 2005/1005; A61N 2005/1018; A61N 5/1002; A61N 5/1001; A61N 5/1007; A61N 5/1014; A61M 25/10; A61M 25/0108; A61M 25/1011
USPC ............ 600/1, 3, 6; 269/266; 604/107, 96.01, 604/101.01, 101.02
See application file for complete search history.

(56) References Cited

U.S. PATENT DOCUMENTS 5,653,683 A * 8/1997 D'Andrea ........................ 604/21
6,068,621 A * 5/2000 Balceta et al. ................. 604/500
(Continued)

OTHER PUBLICATIONS

Dixon Valve Press Release: 2003.*
PCT International Search Report, PCT/US08/04550 filed Apr. 9, 2008, dated Jul. 25, 2008.
PCT Written Opinion, PCT/US08/04550 filed Apr. 9, 2008, dated Jul. 25, 2008.
PCT International Preliminary Report, PCT/US08/04550 filed Apr. 9, 2008, dated Oct. 22, 2009.

*Primary Examiner* — Christine H Matthews
*Assistant Examiner* — Joshua D Lannu
(74) *Attorney, Agent, or Firm* — MacMillan, Sobanski & Todd, LLC

(57) ABSTRACT

A system is provided for use in brachytherapy where a central tube permits passage of a radioactive source therethrough to deliver a prescribed dosage of radiation. One or more balloons are coaxially positioned around the central tube. At least one balloon includes one or more peripheral tubes extending along at least a portion of the balloon. The peripheral tube is also attached to the high dose rate brachytherapy unit in order to permit passage of a radioactive source therethrough.

14 Claims, 4 Drawing Sheets

(56) References Cited

U.S. PATENT DOCUMENTS

| | | |
|---|---|---|
| 6,390,968 B1 | 5/2002 | Harmon |
| 6,699,171 B2 | 3/2004 | Harmon |
| 6,746,465 B2 | 6/2004 | Diederich et al. |
| 2003/0032851 A1* | 2/2003 | Apple et al. ............. 600/3 |
| 2004/0147811 A1 | 7/2004 | Diederich et al. |
| 2006/0014997 A1 | 1/2006 | Kindlein et al. |
| 2006/0020156 A1* | 1/2006 | Shukla ............. 600/3 |
| 2006/0100475 A1* | 5/2006 | White et al. ............. 600/3 |
| 2006/0116546 A1 | 6/2006 | Eng |
| 2007/0106108 A1 | 5/2007 | Hermann et al. |

* cited by examiner

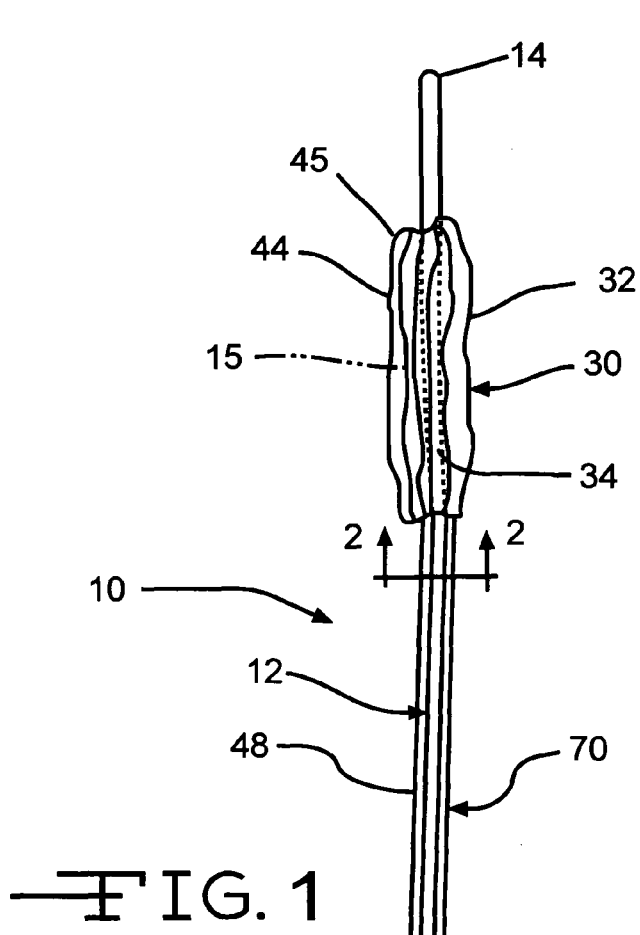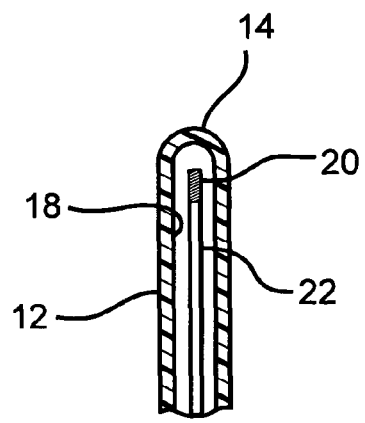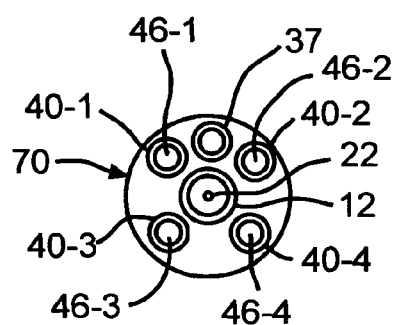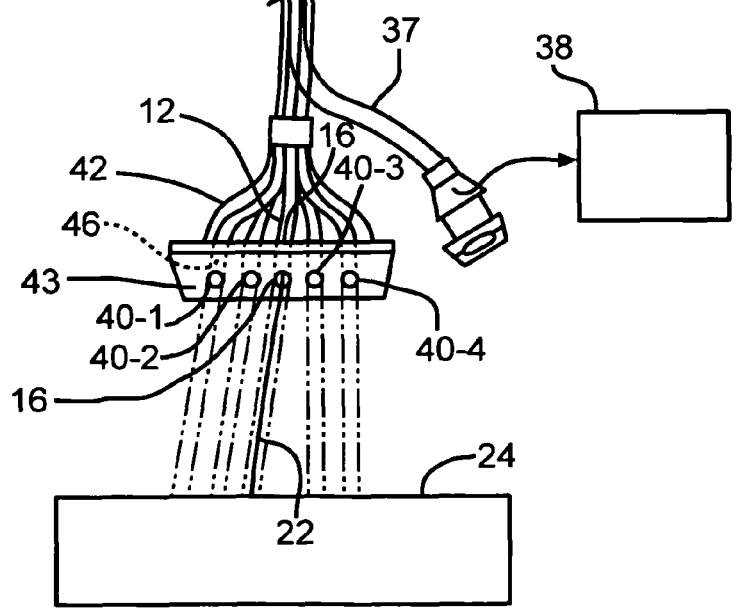
FIG. 1A
FIG. 1
FIG. 2

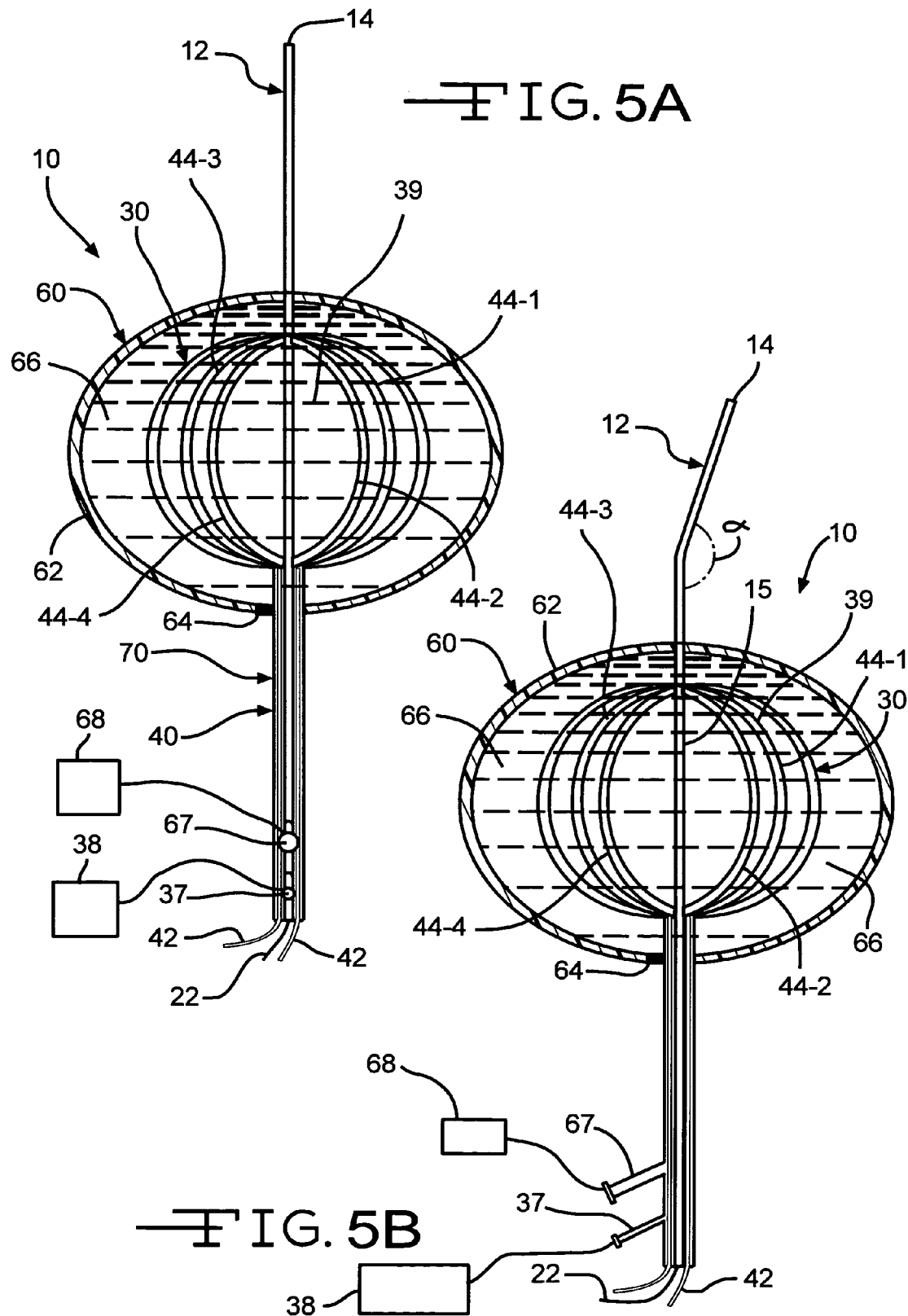

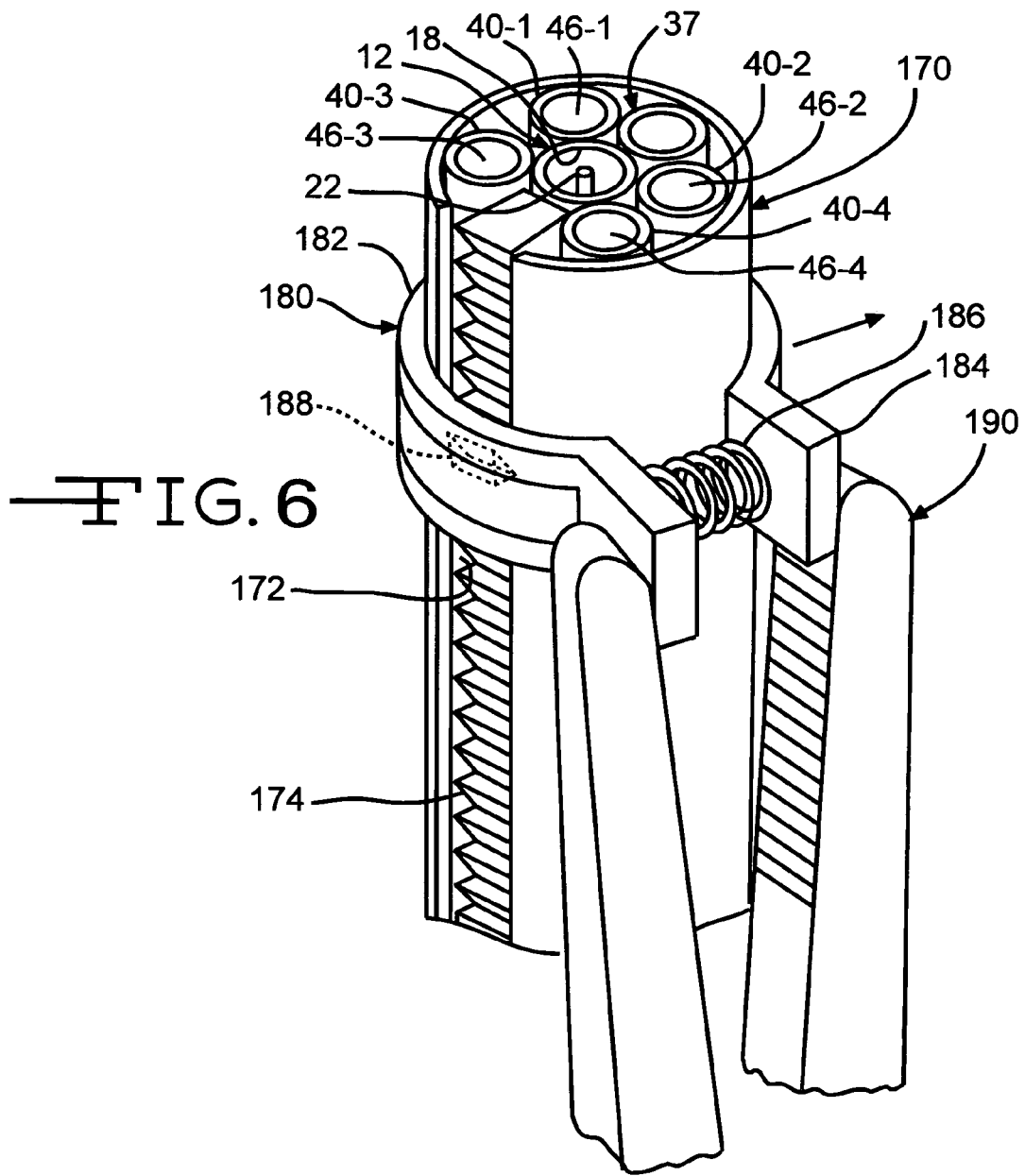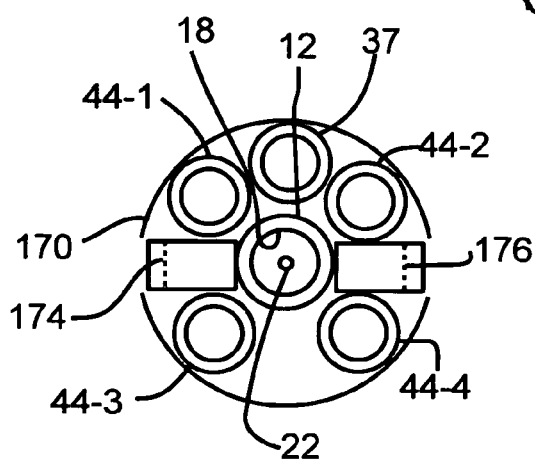

INTRACAVITARY RADIATION SYSTEM

CROSS-REFERENCE TO RELATED APPLICATIONS AND STATEMENT REGARDING SPONSORED RESEARCH

The present invention claims the benefit of the PCT/US2008/004550 filed Apr. 9, 2008, which claims priority the provisional patent application Ser. No. 60/922,726 filed Apr. 10, 2007. This invention was made with no government support and the government has no rights in this invention.

BACKGROUND OF THE INVENTION

For over 50 years, a major component of treatment for uterine cervical cancer (and sometimes uterine body cancer) has consisted of an internal radiation treatment known as brachytherapy. The types of brachytherapy are generally defined by the length of time that the tissue or organ is exposed to a therapeutic radiation source.

Low dose rate (LDR) treatments typically involve several days when the radioactive sources are temporarily placed in tissue. In some cases, permanent or semi-permanent implants may be positioned in the tissue for a much longer period of time.

In contrast, high dose rate (HDR) brachytherapy typically delivers a radiation dosage in a much higher rate than what is administered using LDR brachytherapy. The HDR brachytherapy procedures are therefore, shorter in duration and typically last just a few minutes. In addition to a much higher dose rate, the HDR brachytherapy provides for a precise delivery of the therapeutic radiation. Other advantages of the HDR brachytherapy include the ability to perform the HDR brachytherapy on outpatient basis and improved patient comfort and compliance.

In many HDR brachytherapy procedures, the placement of the radioactive material is automated. An automated HDR brachytherapy device is used to deliver a radioactive source precisely to the tissue or organ in need thereof. The automated HDR brachytherapy procedure is especially useful in the treatment of gynecologic cancers. Often, such treatment plans for HDR brachytherapy require a precise administration of the therapeutic radiation.

It is important that the therapeutic radiation be delivered to the target volume as precisely as possible. In such treatment plans, the clinician must select the optimum sized instrument, based on the individual patient's body configuration and the geometry of the target treatment area. It is especially important to administer a substantially homogeneous dose of radiation to the entire treatment volume, while preventing the irradiation of non-target areas of the patient's body. Thus, while HDR brachytherapy is widely used, the anatomical variations in the shape, thickness, orientation and size of the individual patients, provide challenges to the clinician to deliver a substantially uniform therapeutic radiation dosage.

Further, while HDR brachytherapy has become readily available, the instruments used have not changed substantially. One currently used instrument is a Fletcher-Suite type device that is composed of three components: one tandem and two culpostats or ovoids. The tandem is a narrow metallic cylinder that is introduced into the cervical canal through the vagina. The tip of the tandem is advanced up to the top of the uterine cavity. Part of the tandem exits the vagina to be accessed for source insertion. The two culpostats are cylinders that are attached to a rod-like device that also exits the vagina in a similar fashion to the tandem. The culpostats are inserted into the vagina and advanced to the very top of the vagina, one in the right lateral fornix just next to the external cervical canal and one to the left. These instruments are made of metal and rigid plastic. The culpostats are sized by placing caps over the basic metal culpostat. The largest size of placing caps that the patient can tolerate are inserted. A packing material is placed in the patient above and below the ends of the culpostat to physically displace the closest part of bladder and rectal mucosa away from the radiation source. Just a small movement of the instruments can reduce the radiation dose by as much as one third.

The Fletcher-Suite instrument is placed in surgery with the benefit of anesthesia. Women are admitted to the hospital after the insertion of this instrument, and radioactive sources are manually inserted into the applicator to deliver the radiation dose over 48 to 72 hours. These instruments cause great patient discomfort during the insertion thereof. Also, these instruments generally require the use of packing materials in order to move the bladder and rectum away from the instruments (and thus reduce their radiation exposure). These packing materials also caused great patient discomfort and often presented difficulties for the clinician during insertion thereof.

Thus, what is needed is an improved system to deliver intracavitary doses of radiation.

SUMMARY OF THE INVENTION

In one aspect, there is provided a system and method for administering intracavitary brachytherapy to a patient in need thereof.

In a particular aspect, the applicator includes a central tube having a channel extending therethrough and having a closed distal end and an open proximal end. The central tube is attached to a high dose rate brachytherapy unit. The central tube channel permits passage of a radioactive source through the central tube to deliver a prescribed dosage of radiation.

The applicator also includes a first balloon that is coaxially positioned around at least a mid-section of the central tube. The first balloon can be distended to a desired dimension. The first balloon has a wall that provides the first balloon with an interior chamber having a three-dimensional shape when the balloon is distended to the desired dimension.

The applicator includes one or more peripheral tubes that are also configured to permit passage of a radioactive source therethrough to deliver a prescribed dosage of radiation. The peripheral tube has a proximal section that is attached to the high dose rate brachytherapy unit, and at least one distal section. Thus, the distal section of the more peripheral tube extends along at least a portion of the wall in a generally arcuate manner when the first balloon is distended.

The first balloon is connected to a fluid supply line such that fluid can be supplied to at least partially distend the first balloon. In use, upon distension of the first balloon, at least one of the peripheral distal sections is disposed substantially near a treatment area in a body cavity of a patient.

In another aspect, there is provided an applicator that further includes a second balloon that is at least partially coaxially positioned around the first balloon. The first and second balloon can be independently distended. The second balloon receives a supply of a fluid material sufficient to at least temporarily displace portions of the patient's body not destined to receive brachytherapy.

In yet another aspect, there is provided a method of providing brachytherapy to a patient in need thereof. The method includes positioning at least a portion of one of the brachytherapy applicators described herein substantially adjacent to one or more treatment areas of the patient's body in need of brachytherapy.

In certain embodiments, the first balloon of the brachytherapy applicator can be at least partially distended prior to the positioning of the radiation source in the central tube of the applicator. In other embodiments, one or more radiation sources can be positioned at one or more predetermined locations in the central tube such that a dose of radiation is deliverable to the treatment area thereof prior to at least partially distending the first balloon. Upon inflation of the first balloon, at least one of the peripheral distal sections is disposed substantially near a treatment area of a patient.

In certain embodiments, the first balloon can contain catheters going around the balloon allowing passage of the radiation source. The catheters can be attached to this balloon laterally, (for example at 2 o'clock & 5 o'clock positions) to spare dosing the bladder and rectum).

The method further includes positioning one or more radiation sources at one or more locations in one or more peripheral tubes such that a further dose of radiation is deliverable to the body portion in need thereof.

In embodiments where the brachytherapy applicator further includes a second balloon, the method includes inflating the second balloon. The second balloon can be distended independently of the first balloon. Also, the supply of a fluid to the first balloon can at least partially inflate the second balloon.

Various objects and advantages of this invention will become apparent to those skilled in the art from the following detailed description of the preferred embodiment, when read in light of the accompanying drawings.

BRIEF DESCRIPTION OF THE DRAWINGS

FIG. 1 is a schematic illustration of a side elevational view, partially in cross-section, of one embodiment of a high dosage rate (HDR) brachytherapy applicator.

FIG. 1A is a view, partially in cross-section, of a distal end of a high dosage rate (HDR) brachytherapy applicator.

FIG. 2 is a cross-sectional view taken along the line 2-2 in FIG. 1.

FIG. 5A is a schematic illustration of a side elevational view, partially in cross-section, of another embodiment of a high dosage rate (HDR) brachytherapy applicator in a distended state.

FIG. 5B is a schematic illustration of a lateral elevational view, partially in cross-section, of another embodiment of a high dosage rate (HDR) brachytherapy applicator in a distended state.

FIG. 6 is a schematic perspective illustration of a section of another embodiment of a high dosage rate (HDR) brachytherapy applicator, showing a ratchet device for adjustment of at least one balloon of the applicator.

FIG. 7 is a cross-sectional view of a mid-section of another embodiment of a high dosage rate (HDR) brachytherapy applicator, showing a ratchet device for adjustment of at least one balloon of the applicator.

DETAILED DESCRIPTION OF THE PREFERRED EMBODIMENT(S)

Figure 3:
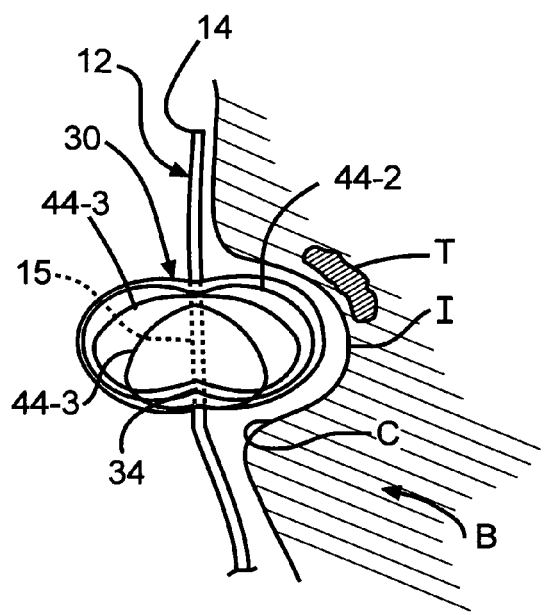
FIG. 3 is a schematic side perspective view, partially in phantom, of a high dosage rate (HDR) brachytherapy applicator in a distended state.

In one aspect, there is provided herein a system and method for administering a high dose rate (HDR) brachytherapy to a patient in need thereof. The embodiments provided for herein describe a system especially useful for performing brachytherapy in a body cavity of a patient in need thereof. In certain embodiments, the system is especially useful for the treatment of gynecological disorders. For ease of illustration, the present system will be generally described in the treatment of cervical and endometrial cancers; however, it should be understood, that other embodiments of the presently described system may be suited to performing HDR brachytherapy in other treatment areas in a patient. Certain embodiments provided for herein may be suited to performing brachytherapy in the uterus of a patient.

As used herein, the term "brachytherapy" generally refers to a radiation therapy procedure in which a source of radiation is placed close to the surface of the body or within a body cavity. The radiation source may include a radioactive liquid, a gel or a radiation seed, and may, for example, be a solid or substantially solid radioactive particle, wire, or the like, that is used as the radiation source during the HDR brachytherapy procedure.

As used herein, the term "body cavity" generally can refer to any inner or open space of a tissue or of a body organ. In one embodiment, a body cavity can refer to a surgically created space within a body or tissue, where, for example, such space was created following the surgical removal of at least a portion of a diseased and/or healthy tissue. In certain embodiments, the body cavity can refer to the interstitial space between two substantially adjacent organs or tissues. In other embodiments, the body cavity can refer to one or more of the natural body cavities such as the patient's vagina or uterus.

The system described herein also reduces exposure of adjacent, non-cancerous tissues and organs to the brachytherapy being administered, thereby reducing and/or preventing complications. The system described herein also enhances patient comfort and tolerance.

Referring now to the Figures, and to FIG. 1 in particular, one embodiment of a HDR brachytherapy applicator 10 is schematically illustrated. The applicator 10 includes at least one central tube 12 having a closed distal end 14, a mid-section 15, and an open proximal end 16. The distal end 14 of the central tube 12 is configured to be positioned substantially adjacent to a distal part of a patient's body cavity during use of the applicator 10, as further explained below. In certain embodiments, at least the distal end 14 of the central tube 12 is made of a flexible material (in certain embodiments, semi-rigid) to allow for easy insertion and manipulation by the clinician.

As shown in FIG. 1A, the central tube 12 defines a channel 18 that is configured to permit passage of a radioactive source 20. In certain embodiments, the radioactive source 20 can be positioned on a wire 22 that is insertable through the channel 18 of the central tube 12. The wire 22 allows the clinician to advance and retract the radioactive source 20 through the channel 18 in the central tube 12 to deliver a prescribed dosage of radiation. In certain embodiments, the closed distal end 14 can be oriented at an angle α with respect to a longitudinally extending axis through the central tube 12, as schematically illustrated in the embodiment shown in FIG. 5B.

At least the open proximal end 16 of the central tube 12 is configured to be attached to a high dose rate (HDR) brachytherapy unit 24. It is to be understood that those skilled in the art recognize that there are different systems by which the open proximal end 16 can be operatively connected to the HDR brachytherapy unit 24 and that such systems are within the contemplated scope of the present invention.

Referring again to FIGS. 1, 3 and 4, the applicator 10 includes a first balloon 30. The first balloon 30 is coaxially positioned around at least a portion of the mid-section 15 of the central tube 12. During use of the applicator 10, the first balloon 30 can be distended or inflated to a desired dimension.

Figure 4:
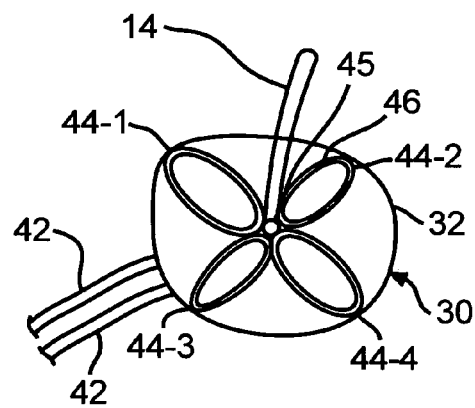
FIG. 4 is a schematic top perspective view, partially in phantom, of a high dosage rate (HDR) brachytherapy applicator in a distended state.

The first balloon 30 includes a wall 32 and at least one input port 34 through which a fluid is introduced, as further explained below. When distended, the wall 32 provides the first balloon 30 with a three-dimensional shape and thus defines an interior chamber of the first balloon 30. While the first balloon 30 is generally shown in its distended state as being spherical in shape (as shown in FIGS. 3 and 4 herein) it is to be understood that the first balloon 30 can generally conform to whatever opening or cavity that surrounds the first balloon 30. In certain embodiments, at least a portion of the wall 32 of the first balloon 30 is made of a material capable of being distended.

Non-limiting examples of suitable materials that are distensible and that may be used in embodiments presented herein are known in the art and may include, but are not limited to, elastomeric materials, including, but not limited to rubbers, silicon rubbers, reinforced rubbers, polymeric films, latex materials or the like. Also, the first balloon 30 can be made of physiologically inert, non-toxic and substantially rupture resistant materials.

In certain embodiments, the radial distance from the wall 32 to the central tube 12 may be substantially uniform along the circumference of the wall 32. In another embodiment, the first balloon 30 may be configured so that the radial distance from the wall 32 to the central tube 12 may be variable along the circumference of the wall 32. In some embodiments, the general shape of the first balloon 30, when distended, may be substantially spherical, while, in other embodiments, the general shape of the first balloon 30, when distended, may be substantially ovoid. In some embodiments, the general shape of the first balloon 30, when distended, may in part be determined by the target body cavity. The three dimensional shape of the distended first balloon 30 helps to ensure that a substantially uniform radiation dosage is administered to the treatment area.

A fluid supply line 37 extends between a fluid reserve 38 and the input port 34 of the first balloon 30. The fluid reserve 38 is configured to hold a fluid 39 that at least partially distends the first balloon 30. It is to be understood that those skilled in the art recognize that there are different systems by which the fluid supply line 37 can be operatively connected to the fluid reserve 38 and the input port 34, and that such systems are within the contemplated scope of the present invention.

In certain embodiments, the first balloon 30 can be distended with a contrast material or radio-opaque material that may be visualized radiologically. In a particular embodiment, the first balloon 30 can be distended with a material that at least partially deflects or absorbs radioactive emissions. Also, absorbing and/or deflecting at least a portion of radiation emitted from the radiation source 20 may be used to at least partially shield surrounding non-treatment areas from some of the deleterious effects of radiation exposure. The fluid may be a liquid and/or gas and may be substantially physiologically inert and non-toxic. In certain embodiments, at least a portion of a fluid may be water or a saline solution.

The applicator 10 also includes one or more peripheral tubes 40. For ease of explanation herein, only one peripheral tube 40 is described in detail. It is to be understood, however, that one or more of the peripheral tubes 40 can have the same features as described herein.

The peripheral tube 40 has a proximal section 42 having an open end 43 and at least one distal section 44 having a closed end 45. The peripheral tube 40 generally defines a channel 46 extending from the open end 43, through a mid-section 48, and terminating at the closed end 45. The peripheral distal section 44 extends along at least a portion of the wall 32 of the first balloon 30, as will be further explained below.

It is within the contemplated scope of the system described herein that at least a portion of the central tube 12 and/or the peripheral tube 40 can be made of a physiologically inert, flexible material. Suitable materials include, but are not limited to, latex, silicone, plastic, polymer, metal, and/or mixtures thereof. Also, in certain embodiments, the central tube 12 can be at least partially made of a material that substantially resists puncture and/or breakage. Also, the central tube 12 is configured such that during insertion in a patient's body, the channel 18 does not substantially collapse.

In a particular embodiment, at least a portion of the central tube 12 may be made of a rigid material. The central tube 12 may be adapted to substantially withstand temperature, pressure, and/or pH changes in a body. In certain embodiments, at least portions of the central tube 12 may be at least partially made of one or more radio-opaque materials. Further, in certain embodiments, at least the distal section 44 of the peripheral tube 40 can be made of an at least longitudinally distensible material. The first balloon 30 can be made of a distensible material, including, but not limited to elastomeric materials.

Still further, in certain embodiments, the central tube 12 and one or more of the peripheral tubes 40 can have markings to allow the location of the radiation source to be accurately positioned adjacent to the treatment area. Also, one or more of the central tube 12 and the peripheral tubes 40 may include radio-opaque markers that facilitate verification of the correct placement of at least a portion of the applicator 10 by using radiological visualization. Such radiological visualization may be used to determine the location and placement of at least a portion of central tube 12 and/or the first and second balloons 30 and 60 in the body cavity, and may include, but are not limited to, X-ray, contrast-enhanced X-ray, computer assisted tomography (CT scan), magnetic resonance imaging (MRI) or ultrasound. The correct placement of the applicator 10 in the body cavity may substantially ensure that an optimal radiation isodose is administered to the treatment area.

Still further one or more of the central tube 12 and the peripheral tubes 40 may have a cross-sectional shape that readily accepts the radiological source 20, and as such, are generally known to one skilled in the art. In some embodiments, central tube 12 and/or the peripheral tubes 40 may have a substantially circular, substantially oval, substantially rectangular, or irregular cross sectional shape. Also, in certain embodiments, the cross-sectional shape of the central tube 12 and/or the peripheral tubes 40 can change along their longitudinal axes. Likewise, the lengths of the central tube 12 and the proximal sections of the peripheral tubes 40 are generally sufficient so that at least a portion thereof resides at a desired site within the patient's body cavity.

Also, the open proximal end 16 of the central tube 12 and the open proximal end 43 of the peripheral tube 40 may be positioned outside the body of the patient so as to be accessible by medical devices used during the procedure and/or by clinicians performing the HDR brachytherapy procedure.

In certain embodiments, one or more of the central tube 12 and the peripheral tubes 40 can be adapted to substantially simultaneously receive one or more radiation sources 20. Receiving multiple radiation sources may include providing the radiation sources to the channel 18 of the central tube 12 and to one or more of the channels 46 of the peripheral tube 40 from the HDR brachytherapy unit 24.

Also, in certain embodiments, it will be readily appreciated by an ordinary practitioner of the art, however, that the channel 18 and/or the channel 46 can be of different lengths, different diameters, and/or adapted to hold different numbers or types of radiation sources. The numbers and configurations of the radiation sources 20 used in a brachytherapy procedure may depend on several factors including but not limited to, the type of tumor, the location of the tumors, the size of the tumor, the size and shape of the body cavity, and the general health of the patient. In one non-limiting embodiment, an HDR brachytherapy procedure may include delivering a therapeutic dosage of radiation to the treatment area.

Referring again in particular to FIG. 1, the open end 43 of the proximal section 42 of the peripheral tube 40 is attached to the high dose rate (HDR) brachytherapy unit 24. It is to be understood that those skilled in the art recognize that there are different systems by which the open end 43 can be operatively connected to the HDR brachytherapy unit 24 and that such systems are within the contemplated scope of the present invention. The peripheral tube 40 is thus configured to permit passage of a radioactive source 20 through the channel 46 of the peripheral tube 40 to deliver a prescribed dosage of radiation to a prescribed treatment area of the patient.

Figure 4A:
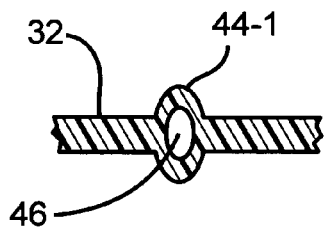
FIG. 4A is a cross-sectional view of one embodiment of a wall and peripheral distal section of a first balloon of a high dosage rate (HDR) brachytherapy applicator.
Figure 4B:
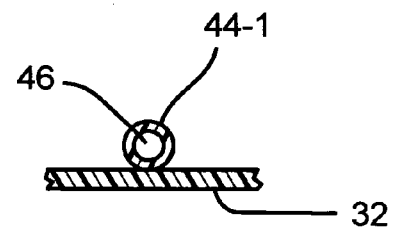
FIG. 4B is a cross-sectional view of another embodiment of a wall and peripheral distal section of a first balloon of a high dosage rate (HDR) brachytherapy applicator.

In certain embodiments, the peripheral distal section 44 can be integrally formed with the wall 32 of the first balloon 30, as shown in FIG. 4A. FIG. 4A is a cross-sectional view showing one embodiment of the wall 32 of the first balloon 30 and the peripheral distal section 44-1 integrally formed as part of the wall 32. Also, in certain embodiments, the peripheral distal section 44 can be positioned on the wall 32 of the first balloon 30. Also, in certain embodiments, the peripheral distal section 44 can be adjacent to and/or adhered to the wall 32 of the first balloon 30, as shown in FIG. 4B. FIG. 4B is a cross-sectional view showing one embodiment of the wall 32 of the first balloon 30 and the peripheral distal section 44-1 adjacent or adhered to the wall 32.

It is to be understood that the peripheral distal section 44 can be in various juxtapositions with respect to the wall 32 and that all such juxtapositions are within the contemplated scope of the system described herein. For ease of explanation herein, the peripheral distal section 44 will be generally referred to as being "on" the wall 32 of the first balloon 30.

In certain embodiments, the first balloon 30 includes multiple peripheral distal sections 44 on the wall 32. In particular embodiments, one or more of the peripheral distal sections 44 can be substantially evenly located around the wall 32 with respect to an adjacent peripheral distal section 44. In certain other particular embodiments, one or more of the peripheral distal sections 44 can be located at varying distances from adjacent peripheral distal sections 44. The spacing of the peripheral distal sections 44 around the wall 32 provides the clinician with many options for the precise delivery of the therapeutic radiation dosage.

As schematically illustrated in the perspective illustrations in FIGS. 3 and 4, the distal section 44 forms an arc along the three-dimensional shape of the first balloon 30, as generally defined by the wall 32.

In certain embodiments, the peripheral distal section 44 is made of a distensible material, such that, when the first balloon 30 is distended, the peripheral distal section 44 is also distended to form an arcuate shaped peripheral distal section 44 along the wall 32 of the distended first balloon 30.

Referring now more particularly to FIG. 3, there is shown therein a plurality of peripheral distal sections 44 generally numbered as 44-1, 44-2, 44-3, etc. positioned on the wall 32 of the first balloon 30. At least one of the peripheral distal sections 44-1 is disposed substantially near an inner surface I of a body cavity C of a patient's body B where there is a treatment area T. In the embodiment shown in FIG. 3, each peripheral distal section 44-1, 44-2, 44-3, etc. is substantially evenly positioned around the three-dimensional wall 32 with respect to an adjacent peripheral section 44.

Figure 4C:
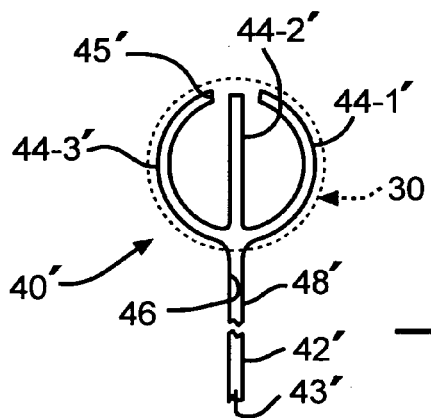
FIG. 4C is a schematic illustration, partially in phantom, of another embodiment of a peripheral tube of a high dosage rate (HDR) brachytherapy applicator.

In a particular embodiment, as schematically illustrated in FIG. 4C, a peripheral tube 40' can have one proximal section 42' having an open end 43' and a plurality of peripheral distal sections 44-1', 44-2', 44-3', etc., each having a closed end 45'. In such embodiment, the peripheral tube 40' generally defines a multi-branched channel 46' extending from the open end 43' to each closed end 45'. Each peripheral distal section 44' extends along at least a portion of the first balloon 30'.

In a similar manner as described above, the open end 43' of the proximal section 42' is attached to the high dose rate (HDR) brachytherapy unit 24. It is to be understood that those skilled in the art recognize that there are different systems by which the open end 43' can be operatively connected to the HDR brachytherapy unit 24 and that such systems are within the contemplated scope of the present invention. The peripheral tube 40' is thus configured to permit passage of a radioactive source 20 through the multi-branched channel 46' to deliver a prescribed dosage of radiation to a prescribed treatment area of the patient.

Further, as fully explained above, one or more of the peripheral distal sections 44' can be positioned on the wall 32 of the first balloon 30'. Also, in certain embodiments, the peripheral distal sections 44' can be integrally formed with the wall 32' of the first balloon 30'. Also, in certain embodiments, one or more of the peripheral distal sections 44' can be adjacent to and/or adhered to the wall 32' of the first balloon 30'. It is to be understood that the peripheral distal sections 44' can be in various positions with respect to the wall 32' and that all such juxtapositions are within the contemplated scope of the system described herein.

Likewise, in certain embodiments, one or more of the peripheral distal sections 44' can be substantially evenly located around the wall 32' with respect to an adjacent peripheral distal section 44'. In certain other particular embodiments, one or more of the peripheral distal sections 44' can be located at varying distances from adjacent peripheral distal sections 44'. The spacing of the peripheral distal sections 44' around the wall 32' provides the clinician with many options for the precise delivery of the therapeutic radiation dosage.

In certain embodiments, the first balloon 30 can contain one or more catheters going around the balloon, thus allowing passage of the radiation source. The catheters can be attached to the balloon laterally (, for example at 2 o'clock & 5 o'clock positions) to spare dosing the bladder and rectum).

Referring now to FIGS. 5A and 5B, there is shown another embodiment of the applicator 10. It is to be noted that, for the same or similar structures as shown in FIGS. 1-4, the same reference numbers will be used for ease of explanation. As such, the applicator 10 in FIGS. 5A and 5B further includes a second balloon 60 that is at least partially coaxially positioned around the first balloon 30.

The second balloon 60 includes a wall 62 and at least one input port 64 through which a fluid is introduced, as further explained below. When distended, the wall 62 provides the second balloon 60 with a three-dimensional shape and thus defines an interior chamber 66 of the second balloon 30. While the second balloon 60 is generally shown FIGS. 5A and 5B herein as being spherical in shape when in its distended state, it is to be understood that the second balloon 60 can generally conform to whatever opening or cavity that substantially surrounds the second balloon 60. In certain embodiments, at least a portion of the wall 62 of the second balloon 60 is made of a material capable of being distended.

Non-limiting examples of suitable materials that are distensible and that may be used in embodiments presented herein for the second balloon 60 are known in the art and may include, but are not limited to, elastomeric materials, including, but not limited to rubbers, silicon rubbers, reinforced rubbers, polymeric films, latex materials or the like. Also, the second balloon 60 can be made of physiologically inert, non-toxic and substantially rupture resistant materials.

The second balloon 60 thus can also be coaxially positioned around at least a portion of the mid-section 15 of the central tube 12. In certain embodiments, the radial distance from the wall 62 to the central tube 12 may be substantially uniform along the circumference of the wall 62.

In another embodiment, the second balloon 60 may be configured so that the radial distance from the wall 62 to the central tube 12 may be variable along the circumference of the wall 62. In some embodiments, the general shape of the second balloon 60, when distended, may be substantially spherical, while, in other embodiments, the general shape of second balloon 60, when distended, may be substantially ovoid. In some embodiments, the general shape of the balloon 60, when distended, may in part be determined by the target body cavity. The three dimensional shape of the distended second balloon 60 also helps to ensure that a substantially uniform radiation dosage is administered to the treatment area.

A fluid supply line 67 extends between a fluid reserve 68 and the input port 64 of the second balloon 60. The fluid reserve 68 is configured to hold the fluid that at least partially distends the second balloon 60. It is to be understood that those skilled in the art recognize that there are different systems by which the fluid supply line 67 can be operatively connected to the fluid reserve 68 and the input port 64, and that such systems are within the contemplated scope of the present invention.

In certain embodiments, the second balloon 60 can be distended with a contrast material or radio-opaque material that may be visualized radiologically. In a particular embodiment, the second balloon 60 can be distended with a material that at least partially deflects or absorbs radioactive emissions. Also, absorbing and/or deflecting at least a portion of radiation emitted from the radiation source 20 may be used to at least partially shield surrounding non-treatment areas from some of the deleterious effects of radiation exposure. The fluid may be a liquid and/or gas and may be substantially physiologically inert and non-toxic. In certain embodiments, at least a portion of a fluid may be water or a saline solution. In certain embodiments, the first, or inner balloon 30, can be filled with a liquid or a gaseous fluid, while the second, or outer balloon 60 is filled with a liquid fluid, preferably with contrast to protect the mucosa from a hot source adjacent to the surrounding tissue.

In certain embodiments, the second balloon 60 can be configured to at least temporarily displace portions of the patient's body not destined to receive the therapeutic brachytherapy. The distension of the first balloon 30 and/or the second balloon 60 may vary according to the volume of fluid delivered thereto, and such volumes may be determined by the clinician performing the HDR brachytherapy procedure. Also, the first balloon 30 and the second balloon 60 can be configured to be independently distended.

In embodiments where the applicator 10 includes the first balloon 30 and the second balloon 60, the first and second balloons 30 and 60, respectively, are substantially co-axially positioned with respect to each other. That is, the volume of the first balloon 30 forms at least a portion of the volume of the second balloon 60. During the use of such applicator 10, either volume can be filled first with the desired fluid.

Referring again to FIG. 1, the peripheral tube 40 includes the mid-section 48 that extends between the peripheral distal section 44 and the open end 43. In a particular embodiment, the applicator 10 can include an outer tubing 70 where at least the mid-sections 48 of the peripheral tubes 40 are gathered. For example, when multiple peripheral tubes 40 are present in the applicator 10, the mid-sections 48 of each peripheral tube 40 can be in a generally parallel alignment, as schematically illustrated in FIG. 2.

Referring now to FIG. 6, a further embodiment of an applicator 10 is schematically illustrated. It is again to be noted that, for the same or similar structures as shown in FIGS. 1-5, the same reference numbers will be used for ease of explanation. In FIG. 6 an outer tubing 170 is at least partially coaxially positioned around the mid-section 15 of the central tube 12 and the mid-sections 48 of one or more peripheral tubes 40. In certain embodiments, at least the mid-sections 48 of each peripheral tube 40 can be in a generally parallel alignment in the outer tubing 170.

The outer tubing 170 includes one or more longitudinally extending grooves 172 that are configured to receive a balloon moving and shaping device 180. In the embodiment shown in FIG. 6, the grooves 172 include a plurality of teeth 174 that are configured to releasably mate with the balloon moving/shaping device 180.

In one embodiment, the balloon moving/shaping device 180 includes a co-axially positioned band 182 having one or more clipping brackets 184 and a spring 186 positioned between opposing brackets 184. The brackets 184 can be at least temporarily moved toward each other by, for example, a needle nosed pliers-type device 190. The band 182 can include one or more mating members 188 on the inner face of the band 182. The mating members 188 are releasably engaged by the teeth 174. During use of the applicator 10, the clinician can ratchet, or move, the band 182 along the longitudinal axis of the outer tubing 170.

In the embodiment shown in FIG. 6, the first balloon 30 and the second balloon 60 are secured to the balloon moving/shaping device 180. The first and second balloons 30 and 60 are co-axially positioned around the band 182. By moving the band 182, the clinician can change the shape of at least one of the second balloon 60 and/or the first balloon 30.

In another embodiment, the band 182 of the balloon moving/shaping device 180 can have a round, donut shape that can be initially advanced by the clinician into the patient's body cavity. The clinician can then inflate the first and second balloons 30 and 60 such that the balloons expand and generally conform to the shape of the patient's body cavity.

FIG. 7 is a cross-sectional view of a further embodiment where the outer tubing 170 includes first and second includes longitudinally extending grooves 172 and 176, respectively, that are configured to receive a movable balloon shaping device 180.

During the use of the applicator 10, the radiation source 20 may be positioned for delivery of the therapeutic dosage in any desired location along the axis defined by the channel 18 in the central tube 12. Also, the radiation source 20 may be positioned for delivery of the therapeutic dosage in any desired location along the arc defined by the channel 46 in the peripheral distal section 44 of the peripheral tube 40.

The positioning of the radiation source 20 in different peripheral tubes 40 and the filling of the first and/or second balloons, 30 and/or 60 respectively, with different volumes of one or more types of fluid, allows the clinician to precisely position the radiation source 20 close to the desired treatment area. In one non-limiting example, independently inflating the second balloon 60 also allows the clinician to provide a shielding material that at least partially absorbs and/or deflects radioactive emissions, thus shielding at least a portion of the non-treatment area from the radiation source 20.

Thus, a HDR brachytherapy procedure may include inserting the distal end 16 of the central tube 12 into the patient's body cavity. The depth to which distal end 16 should be inserted may vary according to each situation and the determination of the appropriate depth is within the skill level of an ordinary clinician. For example, inserting the distal end 16 to the correct location in the body cavity may include using radiological procedures.

Once the distal end 16 of the central tube 12 is properly positioned within the body cavity, the first balloon 30 may be distended with a fluid. In one embodiment, inflating the balloon 30 may cause the body cavity to substantially conform to the three dimensional shape of the distended balloon 30. In another procedure, the first balloon 30 may be only partially distended. It is to be understood that any deflation of the balloon 30 may, in some embodiments, be substantially prevented by engaging one or more stop valves that may be included on the fluid supply line 37.

During the brachytherapy procedure; one or more radiation sources 20 are placed in the central tube 12 and/or the peripheral tubes 40. The number, type and location of radiation sources to be may vary according to each situation. Following administration of the prescribed brachytherapy, the one or more balloons 30 and 60 may be deflated, and the applicator 10 withdrawn from the body. Typically, the applicator 10 described herein will be disposable and is disposed of following its withdrawal from the body cavity.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. An applicator for use in brachytherapy comprising:
a central tube with a closed distal end and configured to be attached to a high dose rate brachytherapy unit so as to permit passage of a radioactive source therethrough to deliver a prescribed dosage of radiation to a tissue or organ in need thereof;
a first balloon having an interior wall positioned about the central tube, the first balloon configured to be selectively distended;
a second balloon that is at least partially positioned about the first balloon, the second balloon configured to be selectively distended to define an interior chamber within which the first balloon is disposed; and
a peripheral tube positioned between the central tube and the first balloon, wherein the peripheral tube does not encompass the central tube and extends along at least a portion of the interior wall of the first balloon, the peripheral tube configured to be attached to the high dose rate brachytherapy unit so as to permit passage of a radioactive source therethrough to deliver a prescribed dosage of radiation to a tissue or organ in need thereof.

2. The applicator defined in claim 1 wherein the peripheral tube is integrally formed with the interior wall of the first balloon.

3. The applicator defined in claim 1 wherein one of the central tube and the peripheral tube has a marking provided thereon that is configured to allow the radioactive source to be accurately positioned.

4. The applicator defined in claim 1 wherein each of the central tube and the peripheral tube has a marking provided thereon that is configured to allow the radioactive source to be accurately positioned.

5. The applicator defined in claim 1 wherein the first balloon and the second balloon are configured to be distended independently of one another.

6. The applicator defined in claim 1 wherein a plurality of peripheral tubes is positioned about the central tube and extend along at least a portion of the interior wall of the first balloon, each of the plurality of peripheral tubes configured to be attached to the high dose rate brachytherapy unit so as to permit passage of a radioactive source therethrough to deliver a prescribed dosage of radiation to a tissue or organ in need thereof.

7. The applicator defined in claim 6 wherein the plurality of peripheral tubes is positioned substantially evenly around the interior wall of the first balloon.

8. The applicator defined in claim 6 wherein each of the plurality of peripheral tubes is integrally formed with the interior wall of the first balloon.

9. The applicator defined in claim 6 wherein one of the central tube and the plurality of peripheral tubes has a marking provided thereon that is configured to allow the radioactive source to be accurately positioned.

10. The applicator defined in claim 6 wherein each of the central tube and the plurality of peripheral tubes has a marking provided thereon that is configured to allow the radioactive source to be accurately positioned.

11. The applicator defined in claim 6 wherein the first balloon and the second balloon are configured to be distended independently of one another.

12. The applicator defined in claim 1 wherein the first balloon is configured to be selectively distended by supplying fluid to an interior chamber of the first balloon.

13. An applicator for use in brachytherapy comprising:
a central tube with a closed distal and configured to be attached to a high dose rate brachytherapy unit and permit passage of a radioactive source therethrough to deliver a prescribed dosage of radiation to a tissue or organ in need thereof;
a first balloon having a wall with an interior facing surface enclosing and facing the central tube, the first balloon configured to be selectively distended by means of a quantity of fluid to an interior chamber of the balloon;
a second balloon that is at least partially positioned about the first balloon, the second balloon configured to be selectively distended to define an interior chamber within which the first balloon is disposed; and
a peripheral tube positioned about the central tube within the first balloon and extending on at least a portion of the interior facing surface of the first balloon, the peripheral tube configured to be attached to the high dose rate brachytherapy unit so as to permit passage of a radioactive source therethrough to deliver a prescribed dosage of radiation to a tissue or organ in need thereof.

14. A combined high dose rate brachytherapy unit and applicator for use in brachytherapy comprising:
  a high dose rate brachytherapy unit; and
  an applicator including:
    a central tube with a closed distal end and attached to the high dose rate brachytherapy unit so as to permit passage of a radioactive source therethrough to deliver a prescribed dosage of radiation to a tissue or organ in need thereof;
    a first balloon having an interior wall positioned about the central tube, the balloon configured to be selectively distended;
    a second balloon that is at least partially positioned about the first balloon, the second balloon configured to be selectively distended to define an interior chamber within which the first balloon is disposed; and
    a peripheral tube positioned between the central tube and the first balloon, wherein the peripheral tube does not encompass the central tube and extends along at least a portion of the interior wall of the first balloon, the peripheral tube attached to the high dose rate brachytherapy unit so as to permit passage of a radioactive source therethrough to deliver a prescribed dosage of radiation to a tissue or organ in need thereof.

* * * * *

UNITED STATES PATENT AND TRADEMARK OFFICE
CERTIFICATE OF CORRECTION

PATENT NO. : 8,961,383 B2  
APPLICATION NO. : 12/595329  
DATED : February 24, 2015  
INVENTOR(S) : E. Ishmael Parsai and John J. Feldmeier Page 1 of 1

It is certified that error appears in the above-identified patent and that said Letters Patent is hereby corrected as shown below:

In the Claims

Column 12, Claim 13, Line 52, after distal insert --end--.

Signed and Sealed this  
Ninth Day of June, 2015

Michelle K. Lee  
*Director of the United States Patent and Trademark Office*